United States Patent [19]

Lang et al.

[11] Patent Number: 5,100,656
[45] Date of Patent: Mar. 31, 1992

[54] PRESERVED HAIR AND BODY TREATMENT COMPOSITIONS AND USE OF A PRESERVATIVE COMBINATION

[75] Inventors: Günther Lang, Reinheim; Hans Hölzel, Fränkisch-Crumbach; Horst Schwarz, Seeheim, all of Fed. Rep. of Germany

[73] Assignee: Wella Aktiengesellschaft, Darmstadt, Fed. Rep. of Germany

[21] Appl. No.: 466,446

[22] PCT Filed: Sep. 21, 1989

[86] PCT No.: PCT/EP89/01092
§ 371 Date: May 17, 1990
§ 102(e) Date: May 17, 1990

[87] PCT Pub. No.: WO90/04382
PCT Pub. Date: May 3, 1990

[30] Foreign Application Priority Data
Oct. 25, 1988 [DE] Fed. Rep. of Germany ....... 3836241

[51] Int. Cl.$^5$ ............................................... A61K 7/075
[52] U.S. Cl. ....................................... 424/70; 424/47; 424/404
[58] Field of Search .......................... 424/70, 47, 404; 514/784, 557

[56] References Cited

U.S. PATENT DOCUMENTS 4,971,784 11/1990 Holzel et al. .................. 424/70

OTHER PUBLICATIONS

Remington's Pharmaceutical Sciences Treatise 1990 Mack Publishing Co. p. 1288.

*Primary Examiner*—Thurman K. Page
*Assistant Examiner*—D. Colucci
*Attorney, Agent, or Firm*—Michael J. Striker

[57] ABSTRACT

The aqueous hair- and body-treatment composition having physiological and dermatological compatibility properties as well as a germ-inhibiting effect contains from 0.1 to 50 percent by weight of a surfactant or a surfactant mixture, from 0.01 to 2.0 percent by weight of sodium formate, ammonium formate, potassium formate or magnesium formate, from 0.05 to 2.0 percent by weight of a sorbic acid element selected from the group consisting of sorbic acid and salts of sorbic acid, including alkali metal salts of sorbic acid, particularly sodium sorbate, and from 0.1 to 1.5 percent by weight of phosphoric acid or an aliphatic organic acid containing from 2 to 6 carbon atoms and being free of amino and halogen substituents. A method of preserving an aqueous hair- and body-cleaning composition is also described.

13 Claims, No Drawings

PRESERVED HAIR AND BODY TREATMENT COMPOSITIONS AND USE OF A PRESERVATIVE COMBINATION

BACKGROUND OF THE INVENTION

The present invention relates to an improved method of preserving hair and body treatment compositions and preserved hair and body treatment compositions.

Hair and body treatment compositions generally contain a preservative which is supposed to effectively protect the composition from infection by microorganisms.

Conflicting demands are made on a preservative for use in hair and body treatment compositions. Thus, on the one hand, it should be favorably tolerated in physiological and dermatological respects and, on the other hand, should possess a good germ inhibiting or even germ killing action. These two demands are usually very difficult to reconcile.

The usual preservatives used in hair and body treatment compositions are e.g. formaldehyde (a), 5-bromo-5-nitro-1,3-dioxane (b), p-hydroxybenzoic acid ester (c), 2,4,4,-trichloro-2,-hydroxydiphenylether (d), 5-chloro-2-methyl-3-isothiazolone (e), 2-methyl-3-isothiazolone (f), and 2-bromo-2-nitropropane-1,3-diol (g).

Recently, some preservatives, such as formaldehyde and 2-methyl-3-isothiazolone, have been suspected of not being sufficiently tolerated. It is known with respect to aldehydes and phenols having a preservative action that they react with proteins or interact with them in a denaturating manner. In addition, there is the risk of sensitization with aldehydes.

Another risk of using such preservatives is the danger of nitrosamine formation. In raw materials containing nitro groups ((b)+(g)), this risk is particularly high when they are used together with other nitrogen-containing components of the cosmetic composition.

Preservatives which do not have the aforementioned disadvantages have already been suggested.

For example, a hair and body cleansing composition is described in DE-OS 3 644 473 which contains a physiologically tolerated salt of formic acid, salicylic acid or its salt, and a physiologically unobjectionable organic or inorganic acid.

However, the use of salicylic acid as preservative is not completely satisfactory, since the salicylic acid can lead to skin rashes with very sensitive people or in exceptional cases to asthma attacks. Moreover, they have a keratolytic effect when used in higher concentrations, which means that they can dissolve the callous layer of the skin.

SUMMARY OF THE INVENTION

Therefore, it is an object of the present invention to provide a hair and body treatment composition containing a combination of preservatives which has a good preservative action, is better tolerated physiologically than the usual preservatives used in such compositions, and which avoids the disadvantages of salicylic acid mentioned above.

It has been found that an aqueous hair and body treatment composition with a content of 0.1 to 50 percent by weight of a surfactant or a surfactant mixture characterized in that it contains a combination of
(A) a physiologically tolerated salt of formic acid,
(B) sorbic acid and/or its physiologically tolerated salt, and
(C) one or more physiologically tolerated inorganic or saturated aliphatic organic acids,
has achieved this object in an outstanding manner.

Sorbic acid is found in nature in the rowanberry (Sorbus aucuparia).

The composition, according to the invention, is better preserved by means of the combination of preservatives described above than the hair and body cleansing composition containing salicylic acid described in DE-OS 3 644 473.

For this reason, the applied concentration of the new preservative system comprising components (A)-(C) can be clearly lower than in the case of DE-OS 3 644 473, so that a better compatibility is achieved simultaneously.

Whereas e.g. a hair and body treatment composition, according to DE-OS 3 644 473, which contains 0.05 percent by weight sodium formate and 0.05 percent by weight salicylic acid is no longer sufficiently preserved, the same composition preserved with 0.05 percent by weight sodium formate and 0.05 percent by weight sorbic acid surpasses the demands of the preservative test.

This is particularly surprising because sorbic acid alone, in low concentrations, does not sufficiently preserve cosmetic compositions, but is irritating to the skin in higher concentrations, e.g. according to H. Janistyn, Handbook of Cosmetics and Scents [Handbuch der Kosmetika und Reichstoffe], volume I, pages 396–397, Dr. A. Hüthig Verlag, Heidelberg (1975).

The benefits of preserving the hair and body treatment composition described above were established by the preservative stress test described in The United States Pharmacopeia, 21st edition (1985), page 1151. The hair treatment composition was contaminated with the microorganisms *Candida albicans* (ATCC No. 10231), *Aspergillus niger* (ATCC No. 16404), *Escherichia coli* (ATCC No. 8739), *Pseudomonas aeruginosa* (ATCC No. 9027), and *Staphylococcus aureus* (ATCC No. 6538) and the development of the germ count was monitored over a period of 28 days.

Whereas the use of sodium formate or sorbic acid alone does not lead to a satisfactory preserving of the hair and body treatment composition, particularly when infected by fungi such as *Aspergillus niger*, the compositions are very well preserved, also against fungi, by means of the use of the combination of preservatives (A), (B) and (C) described above.

Suitable physiologically tolerated salts of formic acid (A) are e.g. sodium formate, ammonium formate, potassium formate, and magnesium formate, wherein the sodium formate is preferred.

Component (A) is contained in the hair and body treatment composition in a quantity of approximately 0.01 to 2.0 percent by weight, preferably 0.1 to 1.0 percent by weight.

Component (B) is contained in the composition, according to the invention, in a quantity of approximately 0.05 to 2.0 percent by weight, preferably 0.1 to 1.0 percent by weight, wherein an alkali sorbate, particularly sodium sorbate, is suitable as salt of the sorbic acid.

Physiologically unobjectionable saturated aliphatic organic acids of component (C) coming into consideration are preferably saturated aliphatic organic acids which are free of amino and halogen substituents and have 2 to 6 carbon atoms, e.g. citric acid, tartaric acid, lactic acid, adipic acid, glyoxylic acid, gluconic acid and malic acid, wherein citric acid is preferred, while phosphoric acid is preferably used as inorganic acid of component (C).

Component (C) is contained in the new compositions in a quantity of approximately 0.1 to 1.5 percent by weight, preferably 0.25 to 0.5 percent by weight.

With component (C), the pH value of the hair and body treatment composition is adjusted to 2.0 to 7.0, preferably 3.0 to 5.8.

The hair and body treatment composition, according to the invention, is preferably in the form of an aqueous solution or emulsion, a lotion, a gel, a cream or an aerosol, and contains, in addition to the combination of (A), (B) and (C), at least one anionic, cationic, nonionogenic or amphoteric surfactant in a quantity of approximately 0.1 to 50 percent by weight, preferably 10 to 25 percent by weight.

The following are mentioned by way of example as surfactants suitable for the new hair and body treatment composition:

a) the alkali-, alkaline earth-, ammonium- or alkanol amine salts of alkane sulfonates, alkyl sulfonates and alkyl ether sulfates, $C_{12}$ to $C_{18}$-alkyl- and particularly $C_{12}$ to $C_{14}$-alkyl sulfate sodium salts or -triethanol-amine salts, sodium- or triethanol amine salts of lauryl- or tetradecyl ether sulfates, disodium salt of the sulfosuccinic hemiester of alkanol amides, soaps and polyether carboxylic acids;

b) the nonionic surface-active agents such as oxethylated fatty alcohols with 12 to 18 carbon atoms, e.g. with up to 40 moles ethylene oxide per mole of fatty alcohol oxethylated lauryl-, tetradecyl-, cetyl-, oleyl-, and stearyl alcohols, alone or in combination; the fatty alcohols of oxethylated lanolin or oxethylated lanolin; polyglycol ethers of saturated or unsaturated fatty alcohols and alkylphenols with 8 to 30 carbon atoms in the alkyl radical and 1 to 10 glyceryl units in the molecule; fatty acid alkanol amides and oxethylated sorbitane fatty acid esters;

c) the cationic surface-active agents such as dilauryl-dimethyl ammonium chloride, the chlorides or bromides of alkyl dimethylbenzyl ammonium, the alkyl trimethyl ammonium salts, e.g. cetyl trimethyl ammonium chloride or bromide, tetradecyl trimethyl ammonium chloride or bromide, alkyl dimethyl hydroxyethyl ammonium chlorides or bromides, dialkyl dimethyl ammonium chlorides or bromides, alkylpyridinium salts, e.g. lauryl- or cetylpyridinium chloride, alkyl amide ethyl trimethyl ammonium ether sulfates, imidazoline derivatives, compounds with a cationic character such as amino oxides, e.g. alkyl dimethyl amino oxides or alkyl aminoethyl dimethylamino oxides;

d) the amphoteric or zwitterionic surface-active agents such as the carboxyl derivatives of imidazole, N-alkyl betaines, N-alkyl amido betaines, N-alkyl sulfobetaines, N-alkyl amino propionates, alkyl dimethyl ammonium acetates, $C_{12}$ to $C_{18}$-alkyl dimethyl carboxymethyl ammonium salts and fatty acid alkyl amido betaines, e.g. dimethyl carboxymethylene propylene amido stearate betaine.

Of course, the composition, according to the invention, can also contain conventional cosmetic additions in addition to the aforementioned components, e.g. perfume oils in a quantity of approximately 0.5 to 5.0 percent by weight, opacifiers, e.g. ethylene glycol distearate, in a quantity of approximately 0.5 to 5.0 percent by weight, pearlescent agents, e.g. a mixture of fatty acid monoalkylol amide and ethylene glycol distearate, in a quantity of approximately 1.0 to 10.0 percent by weight, thickeners such as coconut fatty acid diethanol amide in a quantity of approximately 0.5 to 10.0 percent by weight, thinning agents such as 1,2-propylene glycol, lower aliphatic alcohols or ethoxylated sorbitane monolaurate in a quantity of approximately 0.5 to 5.0 percent by weight, buffers such as sodium citrate or sodium phosphate, in a quantity of approximately 0.1 to 1.0 percent by weight, solubilizers such as e.g. ethoxylated, possibly hydrogenated castor oil, in a quantity of approximately 0.1 to 1.0 percent by weight, as well as dyestuffs such as fluorescein sodium salt in a quantity of approximately 0.1 to 1.0 percent by weight, and hair and skin care additives such as fatty acid esters, fatty alcohols, fatty acid glycerides, ethoxylated or propoxylated saturated fatty alcohols, natural, modified natural or synthetic polymers, e.g. cellulose derivatives, cationic cellulose derivatives, chitosan, cationic chitosan derivatives or polymerizates of acrylic acid and/or their derivatives, grooming materials such as lanolin derivatives, cholesterin and pantothenic acid in a quantity of approximately 0.1 to 10 percent by weight, as well as physiologically tolerated inorganic salts such as sodium chloride, and also moisturizers, dyestuffs, light-protection agents, antioxidants, complexing agents and anti-dandruff ingredients.

Other conventional components known for such compositions which can be contained in the new composition are described e.g. in H. Janistyn, "Handbook of Cosmetics and Scents" [Handbuch der Kosmetika und Reichstoffe], volume 3, (1973), pages 228–284 and 442–462, K. Schrader, "Foundations and Formulas of Cosmetics" [Grundlagen und Rezepturen der Kosmetika], (1979), pages 375–401 and 445–455, and G. A. Nowak, "Cosmetic Preparations" [Die kosmetischen Präparate], (1984), pages 452–512.

The following examples should explain the subject matter of the invention in more detail without limiting it to the examples.

HAIR AND BODY TREATMENT COMPOSITION

EXAMPLE 1

Shampooing composition

| | |
|---|---|
| 0.1 g | sorbic acid |
| 0.1 g | sodium formate |
| 40.0 g | lauryl alcohol diglycol ether sulfate, sodium salt (28 percent, aqueous solution) |
| 0.5 g | perfume oil |
| 4.5 g | sodium chloride |
| 54.7 g | water |
| 100.0 g | |

The pH value is adjusted to 4.8–5.8 with diluted soda lye. The present composition is preserved very favorably and is very well tolerated.

EXAMPLE 2

Shower bath composition

| | |
|---|---|
| 0.2 g | sorbic acid |
| 0.1 g | sodium formate |
| 22.0 g | lauryl alcohol diglycol ether sulfate, sodium salt (70 percent, aqueous solution) |
| 1.0 g | ethylene glycol distearate |
| 3.0 g | coconut fatty acid diethanolamide |
| 1.0 g | perfume |

-continued

| | |
|---|---|
| 0.1 g | phosphoric acid |
| 72.6 g | water |
| 100.0 g | |

The pH value is adjusted to 4.8–5.8 with diluted soda lye. The present composition is very well preserved and excellently tolerated.

EXAMPLE 3

Hair strengthener

| | |
|---|---|
| 1.0 g | sorbic acid |
| 0.2 g | sodium formate |
| 1.0 g | chitosan, low-viscosity (deacetylated to 80 percent) |
| 7.0 g | ethanol |
| 0.1 g | citric acid |
| 90.7 g | water |
| 100.0 g | |

For dissolution (salt formation) of the chitosan as well as for preserving. The present composition is excellently preserved and very well tolerated.

EXAMPLE 4

Hair treatment composition - rinse

| | |
|---|---|
| 0.10 g | sorbic acid |
| 0.10 g | sodium formate |
| 1.00 g | stearyl alcohol |
| 1.00 g | vaseline |
| 0.50 g | self-emulsifying glycerin monodistearate |
| 0.25 g | cetyl trimethyl ammonium chloride |
| 0.10 g | citric acid |
| 96.95 g | water |
| 100.00 g | |

The pH value is adjusted to 2.5–3.5 with citric acid. The present composition is excellently preserved and tolerated.

The percentages given in the present application are percent by weight unless otherwise indicated.

While the invention has been illustrated and described as embodied in preserved hair and body treatment compositions and a method of preserving hair and body treatment compositions, it is not intended to be limited to the details shown, since various modifications may be made without departing in any way from the spirit of the present invention.

Without further analysis, the foregoing will so fully reveal the gist of the present invention that others can, by applying current knowledge, readily adapt it for various applications without omitting features that, from the standpoint of prior art, fairly constitute essential characteristics of the generic or specific aspects of this invention.

What is claimed is new and desired to be protected by Letters Patent is set forth in the appended claims:

1. An aqueous hair- and body- treatment composition having physiological and dermatological compatibility properties as well as a germ-inhibiting effect, said composition containing from 0.1 to 50 percent by weight of a member selected form the group consisting of a surfactant and a surfactant mixture, from 0.01 to 2.0 percent by weight of a salt of formic acid selected from the group consisting of sodium formate, ammonium formate, potassium formate and magnesium formate, from 0.05 to 2.0 percent by weight of a sorbic acid element selected from the group consisting of said sorbic acid and salts of sorbic acid including alkali metal salts of said sorbic acid, and from 0.1 to 1.5 percent by weight of a member of the group consisting of phosphoric acid and aliphatic organic acids containing from 2 to 6 carbon atoms and being free of amino and halogen substituents.

2. A composition according to claim 1, wherein said salt of said formic acid comprises sodium formate.

3. A composition according to claim 1, which contains 0.1 to 1.0 percent by weight of said salt of said formic acid.

4. A composition according to claim 1, which contains 0.1 to 1.0 percent by weight of said sorbic acid element.

5. A composition according to claim 1, in which said sorbic acid element comprises sodium sorbate.

6. A composition according to claim 1, which has a pH value of 2.0 to 7.0.

7. Composition according to claim 1, which has a pH value of 3.0 to 5.8.

8. A composition according to claim 1 in which said aliphatic organic acid is a member selected from the group consisting of citric acid, tartaric acid, lactic acid, adipic acid, malic acid, glyoxylic acid and gluconic acid.

9. A composition according to claim 1, in which said aliphatic organic acid comprises citric acid.

10. A composition according to claim 1, containing 0.25 to 0.5 percent by weight of said member of said group consisting of said phosphoric acid and said aliphatic organic acids.

11. A composition according to claim 1, containing 10 to 25 percent by weight of said surfactant.

12. A method of preserving a hair- and body-cleaning composition which comprises adding thereto a germ-inhibiting composition with physiological and dermatological compatibility properties, said composition containing from 0.01 to 2.0 percent by weight of a salt of formic acid selected from the group consisting of sodium formate, ammonium formate, potassium formate and magnesium formate, from 0.5 to 2.0 percent by weight of a sorbic acid element selected from the group consisting of said sorbic acid and salts of sorbic acid including alkali metal salts of said sorbic acid, and from 0.1 to 1.5 percent by weight of a member of the group consisting of phosphoric acid and aliphatic organic acids containing from 2 to 6 carbon atoms and being free of amino and halogen substituents.

13. A method of preserving a hair- and body-cleaning composition which comprises adding thereto a germ-inhibiting composition with physiological and dermatological compatibility properties, said composition containing from 0.01 to 2.0 percent by weight of a salt of formic acid, from 0.05 to 2.0 percent by weight of a sorbic acid element selected from the group consisting of said sorbic acid and salts of sorbic acid, and from 0.1 to 1.5 percent by weight of a member of the group consisting of phosphoric acid and aliphatic organic acids containing from 2 to 6 carbon atoms and being free of amino and halogen substituents.

* * * * *

UNITED STATES PATENT AND TRADEMARK OFFICE
CERTIFICATE OF CORRECTION

PATENT NO. : 5,100,656

DATED : March 31, 1992

INVENTOR(S) : Gunther Lang, et al

It is certified that error appears in the above-identified patent and that said Letters Patent is hereby corrected as shown below:

Column 6, line 46, replace "from 0.5 to 2 percent" with
--from 0.05 to 2.0 percent--.

Signed and Sealed this

Twenty-first Day of September, 1993

Attest:

BRUCE LEHMAN

Attesting Officer     Commissioner of Patents and Trademarks